(12) United States Patent
Zeppelin

(10) Patent No.: US 6,423,070 B1
(45) Date of Patent: Jul. 23, 2002

(54) HIGH SPEED MOTOR FOR THE SURGICAL TREATMENT OF BONES

(76) Inventor: Dieter Von Zeppelin, Georg-Kalb Strasse 29, D-82049 Pullach (DE)

( * ) Notice: Subject to any disclaimer, the term of this patent is extended or adjusted under 35 U.S.C. 154(b) by 0 days.

(21) Appl. No.: 09/709,396

(22) Filed: Nov. 13, 2000

(30) Foreign Application Priority Data

Nov. 13, 1999 (DE) .......................................... 199 54 717

(51) Int. Cl.$^7$ .............................................. A61B 17/32
(52) U.S. Cl. .......................... 606/79; 606/80; 606/170; 606/180
(58) Field of Search .............................. 606/79, 100, 86, 606/180, 167, 169, 170, 171, 84, 80; 433/105, 127

(56) References Cited

U.S. PATENT DOCUMENTS

| 2,878,809 | A | * | 3/1959 | Treace |
| 3,835,858 | A | * | 9/1974 | Hagen |
| 3,847,154 | A | * | 11/1974 | Nordin |
| 4,071,029 | A | * | 1/1978 | Richmond et al. |
| 4,646,738 | A | * | 3/1987 | Trott |
| 5,057,112 | A | * | 10/1991 | Sherman et al. |
| 5,628,763 | A | * | 5/1997 | Yazawa et al. |

FOREIGN PATENT DOCUMENTS

| DE | 7332292.6 | 11/1973 |
| DE | 7509547.5 | 7/1975 |
| DE | 2722334 | 12/1977 |
| DE | GM 7536182 | 2/1978 |
| DE | 3407199 A1 | 8/1984 |
| DE | 4103663 C2 | 8/1992 |

* cited by examiner

*Primary Examiner*—Pedro Philogene
(74) *Attorney, Agent, or Firm*—Mark M. Friedman

(57) ABSTRACT

The invention relates to a high speed motor for the surgical treatment of bones and microtrepanation, comprising a motor housing 1, 1a and a receiving case 7 for a cutting pin 8, wherein the receiving case 7 is provided with a detachable locking mechanism 9. The motor housing (1, 1a) has an integral and angular construction and is provided with a rest part (4) in the front portion thereof for the user to lay down his fingers.

6 Claims, 1 Drawing Sheet

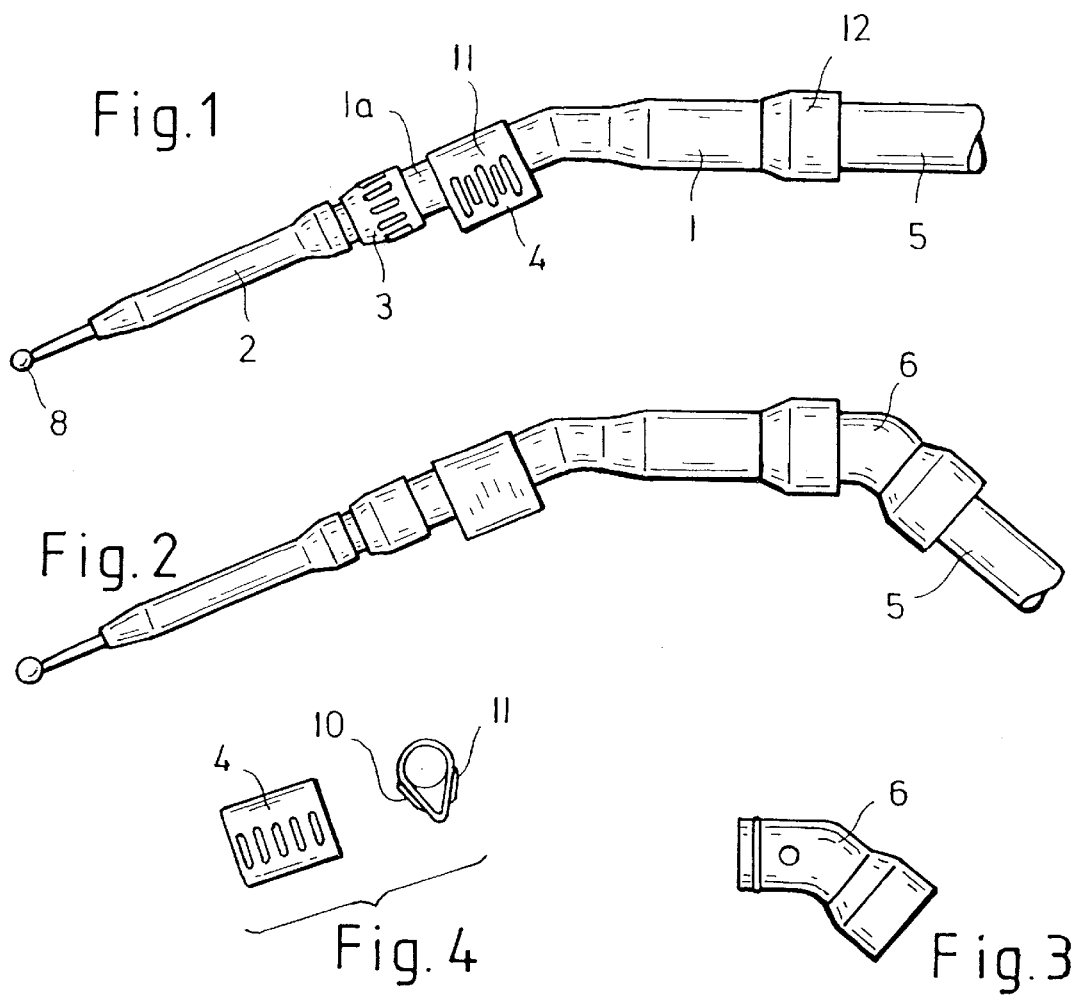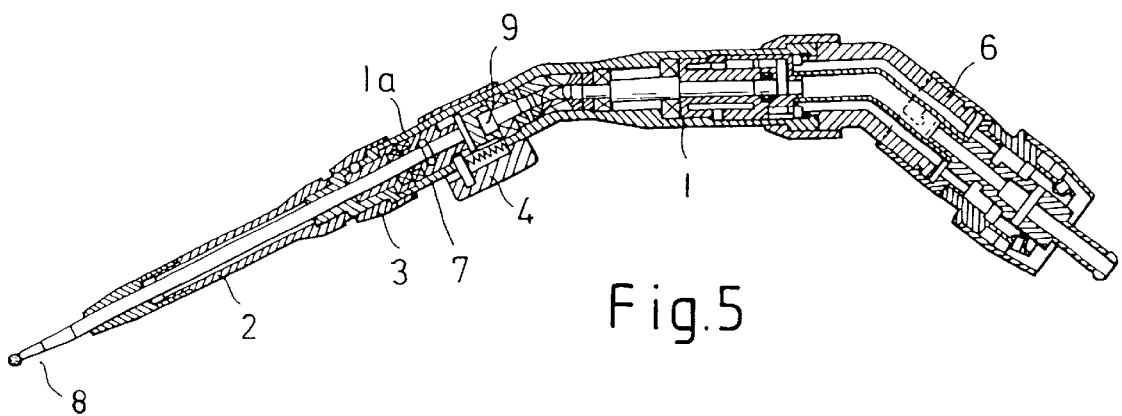

HIGH SPEED MOTOR FOR THE SURGICAL TREATMENT OF BONES

The present invention relates to a high speed motor operated with air pressure, nitrogen or the like for the surgical treatment of bones and for microtrepanation, especially for spinal and cranial operations in neurosurgery, orthopedics and orthorhinolaryngology.

With high speed motors having a number of revolutions of more than 70,000 rpm the bone is removed precisely, fast and without a significant expenditure of energy by the surgeon. During the last decade such systems have increasingly won recognition in the field of microtrepanation. The operative security is substantially increased.

Similar systems are already known, which are operated with air pressure, nitrogen, electric power or the like, and which are used for a similar purpose.

A surgical handpiece is known from DE 41 03 663 C2, which has a straight linear shape.

A surgical instrument especially used for ear surgery is disclosed in DE-OS 27 22 334, which shows a bent housing.

A cutting handpiece comprising a coolant device is known from DE 34 07 199 A1, which is used for the treatment of teeth.

The German utility model 7509547.5 discloses a pneumatically driven surgical rotating instrument having a linear straight structure in the housing area.

A torque transmission device is known from the German utility model 7536182, which likewise has an oblong straight housing structure.

The German utility model 7332292.6 discloses a surgical instrument having a linear elongated housing.

In view of the aforementioned motor drilling systems, however, the handling ergonomics has not sufficiently been taken into account. The mentioned motor drilling systems are partially bulky, involve too much effort in the operation thereof and cause handling problems to the surgeon.

In addition it is disadvantageous that the laborious construction of the known motor drilling systems results in high production costs.

SUMMARY OF THE INVENTION

It is the object of the present invention to provide a high speed motor for the surgical treatment of bones, the design of which is ergonomic and which allows a relaxed, untiring and precise guidance of the working instrument. This is achieved with a high speed motor according to claim 1. The bent construction of the motor housing allows a secure positioning of the high speed motor in the right as well as in the left hand of the user. Thus, the high speed motor according to the invention is located in the user's hand with a firm grip and is stable in view of the position thereof. Due to the integral construction of the motor housing the weight is reduced, resulting in lower manufacturing costs. Instead of several housing parts to be connected with each other, a single integral housing part is required.

PREFERRED EMBODIMENTS OF THE INVENTION

The rest part preferably comprises two rest surfaces provided opposite each other for laying down the thumb or the fingers, respectively. Thus, rest surfaces are provided for the fingers holding the housing, whereby the motor housing is additionally stabilized with regard to its position The rest surfaces are preferably chamfered against each other or extend towards each other so as to provide a secure and precise guidance of the motor between three resting fingers of the user.

The rest part is preferably displaceably mounted and connected to the locking mechanism. The rest part is thereby provided with an additional function and is suited to lock and unlock the inserted cutting pin.

A coupling piece is preferably connected to the rear portion of the motor housing, whereby the coupling piece serves to connect to a power supply line, which is preferably a pressure air connection or the like.

For guiding and covering the cutting pin a shaft cap is preferably provided comprising an enveloping nut, which can be attached to the motor housing. Thus, the cutting pin is effectively guided and protected.

The rest part is preferably adjacent to the enveloping nut without forming an essential gap, when the cutting pin is locked. Thus, the locked state of the cutting pin can be optically controlled.

The angle of the housing of the high speed motor is between 20° and 45°. In said bent region good ergonomics have been found in practice.

One lay-down surface of the rest part preferably serves as a rest for the middle finger and another lay-down surface serves as a rest for the thumb.

The rest part or the lay-down surface thereof is preferably profiled.

The enveloping nut is preferably constructed to serve as a rest for the user's finger tips, and for improving the grip it is preferably provided with a groove profile or the like.

The coupling piece of the high speed motor can preferably be connected to an air hose with two or more hollows or alternatively to an angle adapter.

The angle adapter can preferably be connected to an air hose with two or more hollows.

The connections of the coupling piece and the angle adapter or, respectively, the air hose are preferably produced by means of a pin catch or bayonet catch.

is preferred that the front housing portion has a smaller cross-section than the rear housing portion. This takes into account the fact that by the shoulder for the shaft cap the receiving case can be made essentially slimmer upon the bending. Another advantage resides in the saving of weight due to the smaller diameter and the saving of costs, as no angular shaft caps are required.

Further advantages, features and applications of the present invention can be deduced from the following description of an embodiment in connection with the drawing, wherein FIG. 1 shows a lateral view of an embodiment of a high speed motor according to the invention comprising a straight hose attachment;

FIG. 2 shows a lateral view of an additional embodiment of a high speed motor according to the invention comprising an angled adapter and hose attachment connected thereto;

FIG. 3 shows a lateral view of an angled adapter for use in an embodiment of the invention;

FIG. 4 shows a lateral view and a top view of a rest part for use in a high speed motor according to the invention;

FIG. 5 shows a cross-section through the embodiment of FIG. 2.

The high speed motor shown in the figures is provided with an integral housing comprising housing portions 1a, 1 connected with an angle therebetweeen. The cross-section of the front housing portion 1a is tapered or smaller compared to the rear housing portion 1. The motor housing 1, 1a includes an angle of approximately 30° and is thereby suited to rest in the hand of a user in a well-balanced manner. This refers to the right and to the left hand of a user.

A rest part 4 is provided in the front housing portion 1a for the user to lay down his fingers, which is shown in greater detail in FIG. 4. Said rest part comprises two rest surfaces 10, 11, which are chamfered to each other or extend towards each other, respectively. It is thereby provided that the thumb lies on the front rest surface 11, while the middle finger rests on the rear rest surface 10 and the index lies on the rounded upper face of the rest part 4. Said fingers are capable of guiding and stabilizing the high speed motor due to the position thereof in a completely relaxed and untiring manner. The center of gravity of the motor hereby comes to rest in the dip of the hand between thumb and index, and the thumb lies towards the thenar eminence on the lay-down surface of the rest part, which has a symmetric construction and is especially designed for this purpose. The rest part is located in the front housing portion in the proximity of the bending is point.

The rest part 4 is, moreover, connected to a locking mechanism for a receiving case 7 for a cutting pin 8, which is likewise provided in the front housing. The receiving case can thereby be locked in a detachable manner, and the inserted cutting pins 8 can be locked and unlocked in a convenient manner. For this purpose, the rest part 4 is mounted in a laterally displaceable manner and is effectively connected with the locking mechanism. By displacing the rest part the cutting pins can, therefore, be exchanged during operation.

For guiding the cutting pins and for covering the same a shaft cap 2 with an enveloping nut 3 connected thereto is provided, as is clearly illustrated in FIG. 1. The enveloping nut 3 and the lay-down surfaces 10, 11 are profiled on the upper surfaces thereof so as to allow a secure handling. The enveloping nut 3 is screwed onto the front end of the housing portion 1a and is fixed thereby. In the locked state of the cutting pin 8 the rest part 4 is adjacent to the enveloping nut 3 in a gap-free manner, while FIGS. 1, 2 show the rest part in its unlocked position for the cutting pin 8 displaced towards the right. Thus, the proper locking state of the cutter 8 can also be assessed optically.

In FIGS. 1, 2, 3 and 5 appear a coupling piece 6 configured to couple a power supply line 5 to the high-speed motor of the present invention.

In its cross-section the rest part has approximately the shape of a stylized isosceles triangle, as can be seen in FIG. 4. It is mounted on the front housing portion in a manner secured against rotation and laterally displaceable, and it is preloaded by a spring in the locking position.

The enveloping nut 3 of the shaft cap 2 is also designed to be a handle for the finger tips, for which purpose it is provided with longitudinal grooves, which are equally provided in the lay-down surfaces 10, 11 of the rest part 4.

The diameter of the front motor housing portion 1a is smaller than 15 mm so as to allow an easy to control working All shaft guides are thereby essentially lighter in weight and less expensive, and the handling is facilitated, as no additional arresting mechanism and also no additional angular gear is required.

For narrow and deep operation accesses it is an advantage to bend the high speed motor also in the rear portion by means of an angle adapter. In the event of deep operations the high speed motor can thereby be held further in the back with the same ergonomic advantage. The additional adapter produces a bent and is connected with the air-supplying hose or, respectively, with an electric connection cable.

What is claimed is:

1. A high-speed motor for the surgical treatment of bones and for microtrepanation, comprising:

a. a one-piece motor housing with a front portion with an axis and a rear portion with an axis, where said front portion axis is divergent from said rear portion axis;

b. a displaceable rest part on said front portion of said motor housing connected to a cutting pin locking mechanism of a cutting pin receiving case, said displaceable rest part including a thumb rest surface and a finger rest surface so that said finger rest surface is disposed substantially opposite said thumb rest surface;

where displacement of said displaceable rest part toggles said cutting pin locking mechanism between a state of being locked and a state of being unlocked.

2. The high-speed motor of claim 1 further comprising:

c. a coupling piece attached to said rear portion of said motor housing configured to allow attachment of a motor driving means supply line.

3. The high-speed motor of claim 1 wherein said divergence of said rear portion axis from said front portion axis is between 20° and 45°.

4. The high-speed motor of claim 1 wherein a cross-section of said front portion of said motor housing is smaller than a cross-section of said rear portion of said motor housing.

5. The high-speed motor of claim 1 further comprising:

d. a shaft cap for guiding and covering a cutting pin contained within a cutting pin receiving case, said shaft cap having an enveloping nut attachable to said motor housing.

6. The high speed motor of claim 5 wherein when said displaceable rest part is in a state of being locked, said displaceable rest part is in substantially gap-free contact with said enveloping nut.

* * * * *